US011739322B2

(12) United States Patent
Gao et al.

(10) Patent No.: US 11,739,322 B2
(45) Date of Patent: Aug. 29, 2023

(54) METHOD FOR GENOME EDITING USING A SELF-INACTIVATING CRISPR NUCLEASE

(71) Applicant: INSTITUTE OF GENETICS AND DEVELOPMENTAL BIOLOGY, CHINESE ACADEMY OF SCIENCES, Beijing (CN)

(72) Inventors: Caixia Gao, Beijing (CN); Huawei Zhang, Shandong Province (CN); Shuai Jin, Beijing (CN)

(73) Assignee: INSTITUTE OF GENETICS AND DEVELOPMENTAL BIOLOGY, CHINESE ACADEMY OF SCIENCES, Beijing (CN)

( * ) Notice: Subject to any disclaimer, the term of this patent is extended or adjusted under 35 U.S.C. 154(b) by 385 days.

(21) Appl. No.: 16/966,538

(22) PCT Filed: Jan. 31, 2019

(86) PCT No.: PCT/CN2019/074088
§ 371 (c)(1),
(2) Date: Jul. 31, 2020

(87) PCT Pub. No.: WO2019/149239
PCT Pub. Date: Aug. 8, 2019

(65) Prior Publication Data
US 2021/0047639 A1 Feb. 18, 2021

(30) Foreign Application Priority Data

Feb. 1, 2018 (CN) .......................... 201810101165.6

(51) Int. Cl.
C12N 15/64 (2006.01)
C12N 15/11 (2006.01)
C12N 9/22 (2006.01)
C12N 15/90 (2006.01)

(52) U.S. Cl.
CPC ................ C12N 15/11 (2013.01); C12N 9/22 (2013.01); C12N 15/902 (2013.01); C12N 2310/20 (2017.05); C12N 2510/02 (2013.01); C12N 2800/80 (2013.01)

(58) Field of Classification Search
None
See application file for complete search history.

(56) References Cited

U.S. PATENT DOCUMENTS

2017/0121693 A1* 5/2017 Liu .......................... A61P 13/02
2018/0073035 A1 3/2018 Gao et al.

FOREIGN PATENT DOCUMENTS

CN 105802991 A 7/2016
CN 106834341 A 6/2017
CN 107177625 A 9/2017
WO 2015/160683 A1 10/2015
WO 2015/189693 A1 12/2015

OTHER PUBLICATIONS

Singhal et al. "Self-inactivating Cas9: a method for reducing exposure while maintaining efficacy in virally-delivered Cas9 applications" 2017 Editas Medicine. (Year: 2017).*
Epstein et al. "Engineering a Self-Inactivating CRISPR System for AAV Vector." Molecular Therapy, Elvesier, May 2016 (Year: 2016).*
Komor, M. et al. Programmable editing of a target base in genomic DNA without double-stranded DNA cleavage. Nature 533, 420-424 (2016). https://doi.org/10.1038/nature17946 (Year: 2016).*
S. Cui, S. Zhang, H. Chen, B. Wang, Y. Zhao and D. Zhi, "The Mechanism of Lipofectamine 2000 Mediated Transmembrane Gene Delivery," Engineering, vol. 4 No. 10B, 2012, pp. 172-175. doi: 10.4236/eng.2012.410B045. (Year: 2012).*
Reardon, Sara. "Welcome to CRISPR's Gene Modified Zoo." Scientific American. Mar. 10, 2016. (Year: 2016).*
Sneed, Annie. "Mail-Order CRISPR Kits allow Absolutely Anyone to Hack DNA." Scientific American. Nov. 2, 2017 (Year: 2017).*
Kleinstiver BP et al., Engineered CRISPR-Cas9 nucleases with altered PAM specificities. Nature. Jul. 23, 2015;523(7561):481-5. doi: 10.1038/nature14592. Epub Jun. 22, 2015. PMID: 26098369; PMCID: PMC4540238. (Year: 2015).*
Luo et al., "Applications of CRISPR/Cas9 technology for targeted mutagenesis, gene replacement and stacking of genes in higher plants", Plant Cell Rep., 2016, vol. 35, pp. 1439-1450.
Hess et al., "Directed evolution using dCas9-targeted somatic hypermutation in mammalian cells", Nat Methods, 2016, vol. 13, No. 12, pp. 1036-1042.

(Continued)

Primary Examiner — Amy M Bunker
Assistant Examiner — Vyoma Shailesh Thakker
(74) Attorney, Agent, or Firm — Troutman Pepper Hamilton Sanders LLP

(57) ABSTRACT

Provided are an improved genome editing system and a method that has high specificity, which are capable of obtaining stable mutation types. The system includes an expression construct including a coding sequence of a gRNA targeting at least one genomic target sequence; an expression construct including a coding sequence of a CRISPR nuclease; and an expression construct including a coding sequence for a gRNA targeting a target sequence within the coding sequence of the CRISPR nuclease. Upon introduction into the cell, the gRNA targeting the at least one genomic target sequence directs the CRISPR nuclease to the at least one genomic target sequence and results in one or more mutations in the genomic target sequence, and the gRNA targeting a target sequence within the coding sequence of the CRISPR nuclease directs the CRISPR nuclease to the target sequence within the coding sequence of the CRISPR nuclease and results in an inactivating mutation of the CRISPR nuclease.

9 Claims, 3 Drawing Sheets
Specification includes a Sequence Listing.

(56) References Cited

OTHER PUBLICATIONS

Komor et al., "Programmable editing of a target base in genomic DNA without double-stranded DNA cleavage", Nature, 2016, vol. 533, No. 7603, pp. 420-424.
Gaudelli et al., "Programmable base editing of A•T to G•C in genomic DNA without DNA cleavage", Nature, 2017, vol. 551, No. 7681, pp. 464-471.
International Search Report and Written Opinion issued in Application No. PCT/CN2019/074088 dated Apr. 30, 2019.
Butler et al., "Generation and Inheritance of Targeted Mutations in Potato (*Solanum tuberosum* L.) Using the CRISPR/Cas System", PLOS One, vol. 10. No. 12, 2015, pp. 1-12.
Xing et al., "A CRISPR/Cas toolkit for multiplex genome editing in plants", BMC Plant Biology, 2014, vol. 14, No. 327, pp. 1-12.
Pan et al., "CRISPR/Cas9-mediated efficient and heritable targeted mutagenesis in tomato plants in the first and later generations", Scientific Reports, 2016, vol. 6, Article 24765, pp. 1-9.
Luo et al., "Applications of CRISPR/Cas technology for targeted mutagenesis, gene replacement and stacking of genes in higher plants", Plant Cell Rep., 2016, vol. 35, pp. 1439-1450.
Ma et al., "Targeted AID-mediated mutagenesis (TAM) enables efficient genomic diversification in mammalian cells", Nature Methods, 2016, vol. 13, No. 12, pp. 1029-1035.
Nishida et al., "Targeted nucleotide editing using hybrid prokaryotic and vertebrate adaptive immune systems", Science, 2016, vol. 353, Issue 6305, aaf8729.
Petris et al., "Hit and go CAS9 delivered through a lentiviral based self-limiting circuit", Nature Communications, 2017, vol. 8, p. 15334; 9 pages.
Kim et al., "Increasing the genome-targeting scope and precision of base editing with engineered Cas9-cytidine deaminase fusions", Nature Biotechnology, 2017, vol. 35, No. 4, pp. 371-376.
Moore et al., "CRISPR-based self-cleaving mechanism for controllable gene delivery in human cells", Nucleic Acids Research, 2015, vol. 43, No. 2, pp. 1297-1303.
Kleinstiver et al., "High-fidelity CRISPR-Cas9 nucleases with no detectable genome-wide off-target effects", Nature, 2016, vol. 529, No. 7587, pp. 490-495.

* cited by examiner

METHOD FOR GENOME EDITING USING A SELF-INACTIVATING CRISPR NUCLEASE

CROSS-REFERENCE TO RELATED APPLICATIONS

This application is a U.S. National Phase of International Patent Application No. PCT/CN2019/074088, filed on Jan. 31, 2019, which claims priority to Chinese Application No. 201810101165.6, filed Feb. 1, 2018. The entire contents of these applications are incorporated herein by reference in their entirety.

TECHNICAL FIELD

The invention relates to the field of genetic engineering. In particular, the present invention relates to an improved genome editing system and method that has high specificity and is capable of obtaining stable mutation types.

BACKGROUND

Genome editing technology is a genetic engineering technology based on the specific modification of the genome by specific nucleases, which plays an increasingly powerful role in agriculture and medical research. Clustered regular interspaced short palindromic repeats/CRISPR associated is the most widely used genome editing tool. Due to its high efficiency and ease of use, it has caused a worldwide revolution in the field of gene editing.

Although the CRISPR/Cas9 system has a higher efficiency of site-directed modification, the efficiency of single base mutation in the genome is still low. Komor et al. of David Liu's team from Harvard University combined CRISPR/Cas9 with cytosine deaminase to create a single-base editing system that enables efficient replacement of C to T in a site-directed manner[1]. Since then, various single-base editing systems based on deaminase have emerged. TAM (targeted AID-mediated mutagenesis) established by Changxing et al. can also achieve single-base editing by using a fusion of human cytosine deaminase to dCas9 (dCas9-AIDx)[2]. Keiji Nishida et al. fused a cytosine deaminase from Scorpion venom with Cas9 protein and UGI to achieve targeted mutations in mammalian cells with an efficiency of about 15% to 55%[3]. Scientists from Stanford University have fused cytosine deaminase to the MS2 protein, creating a CRISPR-X system that can also result in higher single-base mutation efficiency[4].

A CRISPR-based single base editing system can result in as few as one base substitution at a particular target sequence, but the length of the target sequence would not be changed. That is to say, the mutated target sequence has the same length as the target sequence that has not been mutated, while has one or more different bases. Due to the possibility of off-targeting of the CRISPR system, CRISPR nucleases may bind to and edit target sites that are slightly different from the gRNA. Therefore, with the original gRNA, the single-base editing system may still recognize the target site that has already been base-edited; and further base-editing would occur. The potential risk is that the types of mutations are not stable. Such risks also exist in other genome editing systems.

Therefore, there remains a need in the art for a new genome editing system and method that is highly specific and results in stable mutation types.

BRIEF DESCRIPTION OF THE INVENTION

In one aspect, the invention provides a genome editing system for site-directed modification of at least one genomic target sequence in the genome of a cell, comprising:

1) an expression construct comprising a coding sequence of a gRNA targeting the at least one genomic target sequence;

2) an expression construct comprising a coding sequence of a CRISPR nuclease; and 3) an expression construct comprising coding sequence for a gRNA targeting a target sequence within the coding sequence of the CRISPR nuclease, wherein, upon introduction into the cell, said gRNA targeting the at least one genomic target sequence directs the CRISPR nuclease to said at least one genomic target sequence and results in one or more mutations in the target sequence, and the gRNA targeting a target sequence within the coding sequence of the CRISPR nuclease directs the CRISPR nuclease to said target sequence within the coding sequence of the CRISPR nuclease and results in an inactivating mutation of the CRISPR nuclease.

In another aspect, the invention provides a method of modifying at least one genomic target sequence in the genome of a cell, comprising introducing a genome editing system of the invention into the cell.

In another aspect, the invention also provides a method of producing a genetically modified cell, comprising introducing a genome editing system of the invention into a cell.

In another aspect, the invention also provides a genetically modified organism comprising the genetically modified cell produced by the method of the invention or progeny thereof.

In still another aspect, the invention also includes a kit for use in the method of the invention, wherein the kit comprises the genome editing system of the invention, and an instruction for use.

DETAILED DESCRIPTION OF THE INVENTION

Figure 1:
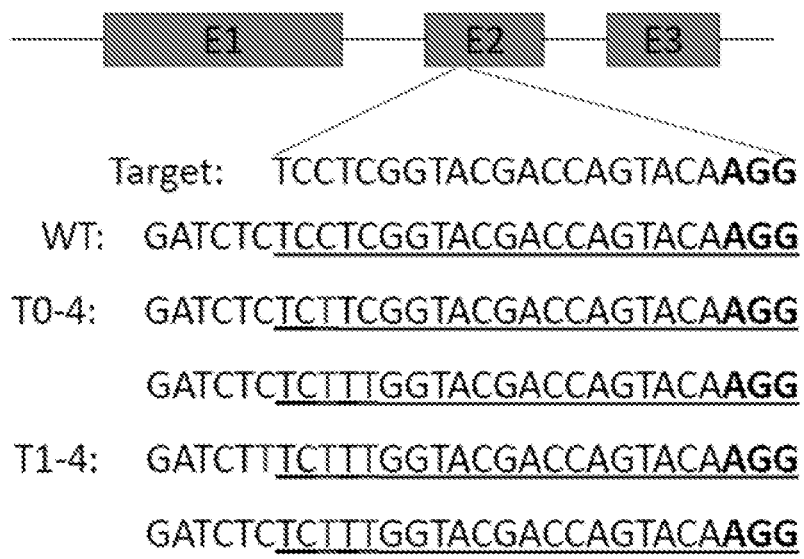
FIG. 1: Genetic analysis of single-base editing mutants of rice OsWxb gene.

In the present invention, unless indicated otherwise, the scientific and technological terminologies used herein refer to meanings commonly understood by a person skilled in the art. Also, the terminologies and experimental procedures used herein relating to protein and nucleotide chemistry, molecular biology, cell and tissue cultivation, microbiology, immunology, all belong to terminologies and conventional methods generally used in the art. For example, the standard DNA recombination and molecular cloning technology used herein are well known to a person skilled in the art, and are described in details in the following references: Sambrook, J., Fritsch, E. F. and Maniatis, T., Molecular Cloning: A Laboratory Manual; Cold Spring Harbor Laboratory Press: Cold Spring Harbor, 1989.

In one aspect, the invention provides a genome editing system for site-directed modification of at least one genomic target sequence in the genome of a cell, comprising:

1) an expression construct comprising a coding sequence of a gRNA targeting the at least one genomic target sequence;

2) an expression construct comprising a coding sequence of a CRISPR nuclease; and 3) an expression construct comprising coding sequence for a gRNA targeting a target sequence within the coding sequence of the CRISPR nuclease, wherein, upon introduction into the cell, said gRNA targeting the at least one genomic target sequence directs the CRISPR nuclease to said at least one genomic target sequence and results in one or more mutations in the target sequence, and the gRNA targeting a target sequence within the coding sequence of the CRISPR nuclease directs the CRISPR nuclease to said target sequence within the coding sequence of the CRISPR nuclease and results in an inactivating mutation of the CRISPR nuclease. For example, said inactivating mutation is a mutation that results in an early termination of translation of the CRISPR nuclease.

The present inventors have found that a CRISPR nuclease-based genome editing system, which has been introduced into a cell and has achieved mutation(s) in the target sequence, will further edit the target sequence that has already been mutated if the genome editing system is still active in the cell (for example, the coding sequence of CRISPR nuclease or gRNA is integrated into the genome and continually expressed), and thereby change the type of mutation in the target sequence, resulting in instable mutations within the obtained cell or organism. In addition, due to the sustained activity of the genome editing system, the possibility of off-target is greatly increased.

This is especially the case for CRISPR-based single base editing systems, which can result in as few as one base substitution at a particular target sequence with the length of the target sequence unchanged (i.e., the mutated target sequence has the same length as the target sequence that has not been mutated, while has one or more different bases). Due to the possibility of off-targeting of the CRISPR system, CRISPR nucleases may bind to and edit target sites that are slightly different from the gRNA. Therefore, with the original gRNA, the single-base editing system may still recognize the target site that has already been base-edited, and further base-editing would occur. The potential risk is that the types of mutations are not stable.

However, the inventors have surprisingly discovered that by adding a gRNA targeting the coding sequence of the CRISPR nuclease in the genome editing system, the CRISPR nuclease in the cell also targets the coding sequence of itself after editing the target sequence, resulting in inactivation of the CRISPR nuclease itself (no longer expressed or expressed as a version without editing activity), which prevents further editing of the target sequence that has been mutated and thus increases the specificity of editing.

As used herein, the term "CRISPR nuclease" generally refers to a nuclease present in a naturally occurring CRISPR system, as well as modified forms thereof, variants thereof, catalytically active fragments thereof, and the like. CRISPR nuclease is capable of interacting with a crRNA and optional a tracrRNA or an artificial gRNA to recognize and/or cleave a target nucleic acid structure. The term encompasses any nuclease based on the CRISPR system that enables genome editing (including base editing) within a cell.

In some embodiments, the CRISPR nuclease includes Cas9 nucleases or variants thereof. The Cas9 nuclease may be a Cas9 nuclease from various species, such as spCas9 from *S. pyogenes*.

In some embodiments, the Cas9 nuclease variant comprises a highly specific variant of Cas9 nuclease, such as the Cas9 nuclease variants eSpCas9 (1.0) (K810A/K1003A/R1060A), eSpCas9 (1.1) (K848A/K1003A/R1060A) of Feng Zhang et al., and the Cas9 nuclease variant SpCas9-HF1 (N497A/R661A/Q695A/Q926A) developed by J. Keith Joung et al.

In some embodiments, the Cas9 nuclease variant comprises a Cas9 nickase (nCas9), wherein one of the two subdomains (HNH nuclease subdomain and RuvC subdomain) of the DNA cleavage domain of Cas9 nuclease is inactivated to form a nickase.

In some embodiments, the CRISPR nuclease include Cpf1 nucleases or variants thereof such as highly specific variants. The Cpf1 nuclease may be a Cpf1 nuclease from various species, such as a Cpf1 nuclease from *Francisella novicida* U112, Acidaminococcus sp. BV3L6, and Lachnospiraceae bacterium ND2006.

In some embodiments, the CRISPR nuclease also comprises a fusion protein of a CRISPR nuclease lacking DNA cleavage activity and a deaminase, also referred to herein as "single-base editing CRISPR nuclease".

As used herein, "a CRISPR nuclease lacking DNA cleavage activity" includes, but is not limited to, Cas9 nickase (nCas9), nuclease-dead Cas9 nuclease (dCas9) or nuclease-dead Cpf1 nuclease (dCpf1). The nuclease-dead Cas9 nuclease (dCas9) or the nuclease-dead Cpf1 nuclease (dCpf1) completely lacks DNA cleavage activity. A number of CRISPR nucleases lacking DNA cleavage activity are known in the art.

As used herein, "deaminase" refers to an enzyme that catalyzes a deamination reaction. In some embodiments of the invention, the deaminase refers to a cytosine deaminase capable of accepting single-stranded DNA as a substrate and capable of catalyzing the deamination of cytidine or deoxycytidine to uracil or deoxyuridine, respectively. In some embodiments of the invention, the deaminase refers to adenine deaminase, which is capable of accepting single-stranded DNA as a substrate and capable of catalyzing the formation of inosine (I) from adenosine or deoxyadenosine (A). Base editing in a target DNA sequence, such as C to T conversion or A to G conversion, can be achieved by using a fusion protein of a CRISPR nuclease lacking DNA cleavage activity and a deaminase ("single-base editing CRISPR nuclease"). A variety of suitable cytosine deaminase or adenine deaminase capable of accepting single-stranded DNA as a substrate are known in the art, such as APOBEC1 deaminase, activation-induced cytidine deaminase (AID), APOBEC3G, CDA1, or for example, DNA-dependent adenine deaminase disclosed by Nicloe M. Gaudelli et al., doi: 10.1038/nature 24644, 2017.

As used herein, "gRNA" and "guide RNA" can be used interchangeably, which refers to an RNA molecule capable of forming a complex with a CRISPR nuclease and capable of targeting the complex to a target sequence due to certain complementarity to the target sequence. For example, in a Cas9-based gene editing system, a gRNA is typically composed of a crRNA and a tracrRNA molecule forming complexes through partial complement, wherein the crRNA comprises a sequence that is sufficiently complementary to a target sequence for hybridization and directs the CRISPR complex (Cas9+crRNA+tracrRNA) to specifically bind to the target sequence. However, it is known in the art that single guide RNA (sgRNA) can be designed, which comprises the characteristics of both crRNA and tracrRNA. The guide RNA of the Cpf1-mediated genome editing system is typically composed only of a mature crRNA molecule, wherein the crRNA comprises a sequence that is sufficiently identical to the target sequence to hybridize to the complement of the target sequence and direct the complex (Cpf1+crRNA) to sequence specifically bind to the target sequence. It is within the ability of those skilled in the art to design suitable gRNA sequences based on the CRISPR nucleases used and the target sequences to be edited.

In a specific embodiment of the invention, the CRISPR nuclease is APOBEC1-nCas9, which is a fusion protein of APOBEC1 deaminase and Cas9 nickase (nCas9). In some embodiments, APOBEC1-nCas9 has the amino acid sequence of SEQ ID NO:1.

In some embodiments, in order to be suitable for designing a suitable gRNA, the coding sequence of the CRISPR nuclease is modified to introduce a PAM sequence and/or a site to be mutated without altering the expression product, and if the site is mutated, the CRISPR nuclease can be inactivated. For example, one or more Cs may be included in the coding sequence of "single-base editing CRISPR nuclease" such that one or more stop codons can be formed when one or more Cs are edited to Ts by single-base editing, through which the translation of the single-base editing CRISPR nuclease is terminated, thereby preventing the continuous production of a functional single-base editing CRISPR nuclease.

For example, in some embodiments, the coding nucleotide sequence of the APOBEC1-nCas9 is shown in SEQ ID NO: 2. Accordingly, the gRNA directed against the coding sequence of the APOBEC1-nCas9 recognizes (targets) the sequence set forth in SEQ ID NO:3.

"Genome" as used herein encompasses not only chromosomal DNA present in the nucleus, but also organellar DNA present in the subcellular components (e.g., mitochondria, plastids) of the cell.

As used in the present invention, "expression construct" refers to a vector such as a recombinant vector that is suitable for expression of a nucleotide sequence of interest in a organism. "Expression" refers to the production of a functional product. For example, expression of a nucleotide sequence may refer to the transcription of a nucleotide sequence (e.g., transcription to produce mRNA or functional RNA) and/or the translation of an RNA into a precursor or mature protein. The "expression construct" of the present invention may be a linear nucleic acid fragment, a circular plasmid, a viral vector. The "expression construct" of the present invention may comprise regulatory sequences and nucleotide sequences of interest from different origins, or regulatory sequences and nucleotide sequences of interest from the same source but arranged in a manner different from that normally occurring in nature. "Regulatory sequence" and "regulatory element" are used interchangeably to refer to a nucleotide sequence that is located upstream (5 'non-coding sequence), middle or downstream (3' non-coding sequence) of a coding sequence and affects the transcription, RNA processing or stability or translation of the relevant coding sequence. Regulatory sequences may include, but are not limited to, promoters, translation leaders, introns and polyadenylation recognition sequences.

Examples of promoters that can be used in the present invention include but are not limited to polymerase (pol) I, pol II or pol III promoters. Examples of pol I promoters include chicken RNA pol I promoter. Examples of pol II promoters include but are not limited to cytomegalovirus immediate early(CMV) promoter, rous sarcoma virus long terminal repeat(RSV-LTR) promoter and simian virus 40(SV40) immediate early promoter. Examples of pol III promoters include U6 and H1 promoter. Inducible promoter such as metalothionein promoter can be used. Other examples of promoters include T7 bacteriophage promoter, T3 bacteriophage promoter, β-galactosidase promoter and Sp6 bacteriophage promoter etc. When used for plants, promoters that can be used include but are not limited to cauliflower mosaic virus 35S promoter, maize Ubi-1 promoter, wheat U6 promoter, rice U3 promoter, maize U3 promoter and rice actin promoter etc.

An "expression construct" of the invention may also comprise a selectable marker for screening a transformed cell or organism, such as an antibiotic resistance marker, a herbicide resistance marker, and the like.

In the present invention, the coding sequence of the gRNA directed against the at least one genomic target sequence, the coding sequence of the CRISPR nuclease, and the coding sequence of the gRNA directed against the CRISPR nuclease may each be constructed in a separate expression construct. Alternatively, they can be constructed in a same construct in any combination. For example, if multiple genomic target sequences are to be edited, coding sequences of the gRNAs directed against these target sequences can be constructed in the same expression construct. Alternatively, for example, a coding sequence of a gRNA directed against a genomic target sequence can be constructed in the same expression construct together with a coding sequence of a gRNA directed against a CRISPR nuclease. Methods of constructing expression constructs for expression of multiple gRNAs are known in the art.

The cells which can be subjected to genome editing with the method of the present invention preferably are eukaryotic cells, include but are not limited to, mammal cells such as cells of human, mouse, rat, monkey, dog, pig, sheep, cow and cat; poultry such as chicken, duck and goose; and cells of plants including monocotyledons and dicotyledons such as rice, maize, wheat, sorghum, barley, soybean, peanut and *Arabidopsis thaliana* etc.

In another aspect, the invention provides a method of modifying at least one genomic target sequence in the genome of a cell, comprising introducing a genome editing system of the invention into the cell.

"Introduction" of a construct of the genome editing system of the invention into a cell means that the construct is used to transform a cell such that the construct is capable of functioning in the cell (e.g., expressing the CRISPR nuclease and/or transcribing the gRNA). As used in the present invention, "transformation" preferably means stable transformation. "Stable transformation" refers to the introduction of exogenous nucleotide sequences into the genome, resulting in the stable inheritance of foreign genes. Once stably transformed, the exogenous nucleic acid sequence is stably integrated into the genome of the organism and any of its successive generations. In some embodiments, stably transformed cells are screened by a selectable marker on the expression construct.

Methods for introducing the genome editing system of the present invention into the cell include, but are not limited to calcium phosphate transfection, protoplast fusion, electroporation, liposome transfection, microinjection, viral infection (such as a baculovirus, a vaccinia virus, an adenovirus and other viruses), particle bombardment, PEG-mediated protoplast transformation or *agrobacterium*-mediated transformation.

In the present invention, the target sequence in the genome of the cell may be located anywhere in the genome, for example, within a functional gene such as a protein-coding gene or, for example, may be located in a gene expression regulatory region such as a promoter region or an enhancer region, and thereby achieve the functional modification of said gene or achieve the modification of gene expression. The mutation in the target sequence in the genome of the cell can be detected by T7EI, PCR/RE or sequencing methods. The mutations may be, for example, a substitution, a deletion and/or an addition.

In another aspect, the invention also provides a method of producing a genetically modified cell comprising introducing a genome editing system of the invention into the cell.

In another aspect, the invention also provides a genetically modified organism comprising the genetically modified cell produced by the methods of the invention or progeny thereof.

"Genetically modified organism" or "genetically modified cell" means an organism or cell that contains an exogenous polynucleotide or modified gene or expression control sequence within its genome. For example, the exogenous polynucleotide is stably integrated into the genome of an organism or cell and inherited for successive generations. The exogenous polynucleotide can be integrated into the genome alone or as part of a recombinant DNA construct. The modified gene or expression control sequence is the sequence in the genome of the organism or cell that comprises single or multiple deoxynucleotide substitutions, deletions and additions. The term "exogenous" with respect to sequence means a sequence that originates from a foreign species, or, if from the same species, is substantially modified from its native form in composition and/or genomic locus by deliberate human intervention.

As used herein, "organism" includes any organism, preferably a eukaryote, suitable for genome editing. The organism includes, but is not limited to mammals such as humans, mice, rats, monkeys, dogs, pigs, sheep, cows and cats; poultry such as chicken, ducks and geese; and plants including monocotyledons and dicotyledons such as rice, maize, wheat, sorghum, barley, soybean, peanuts and *Arabidopsis thaliana*, and the like.

In the genome editing operation of plants, constructs expressing the components for genome editing are preferably integrated into the genome to facilitate screening of transformed plants by selectable markers of the construct, so as to improve the efficiency of obtaining genome-edited plants. However, since the coding sequences of CRSPR nucleases and/or gRNAs are integrated into the plant genome, they will have sustained activity in subsequent generations, and thus there is a risk of further editing of the target sequences that have already been edited (especially in the case of single base editing), as well as higher off-target effect. Thus, the system and method of the present invention are particularly suitable for genetic modification (e.g., genome editing) of plants because the CRSPR nuclease will be inactivated upon completion of editing of the target sequence. Thus, in some preferred embodiments of the invention, the cell is a plant cell. In some preferred embodiments of the invention, the organism is a plant.

In still another aspect, the invention also includes a kit for use in the method of the invention, wherein the kit comprises the genome editing system of the invention, and an instruction for use. A kit generally includes a label indicating the intended use and/or method of use of the contents of the kit. The term label includes any written or recorded material provided in or with the kit.

EXAMPLES

The invention is further illustrated by the following examples, which are not intended to limit the invention.

Example 1. APOBEC1-nCas9 is Capable of Targeting and Further Single-Base Editing a Site where a Single Base Mutation has Occurred The present inventors performed single-base editing on a target site in the Wxb gene of rice by designing a single sgRNA (see FIG. 1). Single base editing was performed using APOBEC1-nCas9 (SEQ ID NO: 1). The sgRNA coding sequence and the APOBEC1-nCas9 coding sequence (SEQ ID NO: 4) were integrated into the rice genome.

A mutant T0-4 was identified in T0 plants, and mutations were made at both alleles of Wxb: in one of the alleles, C at the third position of the target site was mutated to T; in the other allele, the two Cs at the third and fifth positions of the target site were mutated to T.

However, it was surprisingly found that some plants had altered mutation types during the genotyping of the mutant T1 plants. For example, one of the plants, T1-4, an allele was found in which three Cs were mutated to T, and no allele with single C-T mutation in the T0 generation was detected. This indicated that during the passage, the original sgRNA can still mediate APOBEC1-nCas9 to act on the site where base substitution has occurred.

Example 2. Imperfectly Matched sgRNA can Guide APOBEC1-nCas9 for Base Editing

In order to further prove that the edited target site can still be recognized by the original sgRNA and further edited. The inventors designed a set of sgRNAs predicted to be mismatched for verification.

A plurality of tandem Cs are present in a target sequence of the rice OsALS2 gene. The inventors designed multiple sgRNAs, each has a nucleotide that could not pair with the corresponding site of the genomic target sequence. The APOBEC1-nCas9 expression construct and the expression construct of each sgRNA were co-transformed into plants using *Agrobacterium* transformation, and the plants were screened by selectable markers. As a result, there is still a high mutation efficiency in the selected T0 generation. This suggests that mismatched sgRNAs can still direct APOBEC1-nCas9 for single-base editing.

TABLE 1

Efficiency of single base editing mediated by imperfectly matched sgRNA

| No. | Target sequence | Summary (mutants/ total plants) | mutation efficiency |
| --- | --- | --- | --- |
| Target | CAGGTCCCCC GCCGCATGAT | * | * |
| sgRNA-1 | CAGGTCTCCC GCCGCATGAT | 25/41 | 61.0% |
| sgRNA-2 | CAGGTCCTCC GCCGCATGAT | 6/9 | 66.7% |
| sgRNA-3 | CAGGTCCCTC GCCGCATGAT | 17/28 | 60.7% |

Example 3. Development of a New Single Base Editing System

Figure 2:
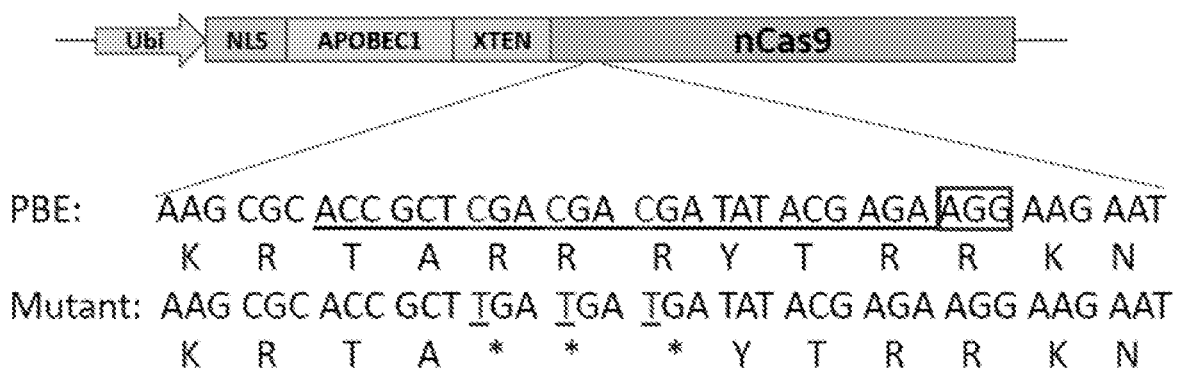
FIG. 2: Working principle of pSU-PBE.

First, the APOBEC1-nCas9 fusion protein was re-encoded at the DNA level (SEQ ID NO: 2): three arginine codons were set to CGA; the next arginine codon was set to AGG, creating a PAM. An sgRNA was designed to recognize the target sequence shown in FIG. 2 (SEQ ID NO: 3). A mutation of C to T in any one of the CGA codons can terminate the translation of the nCas9 protein, preventing the production of a functional fusion protein. We named this set of vectors (including the engineered APOBEC1-nCas9 vector and the corresponding sgRNA vector) as pSU-PBE. The working principle of pSU-PBE is shown in FIG. 2. The black box identifies the PAM site, and the underline identifies the target sequence on the nCas9 gene that the sgRNA is against.

Example 4. A Plant with Edited Genome Target Site and Completely Inactivated BE3 can be Obtained with the Novel Single-Base Editing System The rice OsALS2 gene and OsNRT1.1B were edited using the pSU-PBE system plus a gene-specific sgRNA expression vector. The mutation efficiency is shown in Table 2. When the APOBEC1-nCas9 mutation is homozygous and the target site is mutated, the plants with stably inherited mutation types can be obtained in the T1 generation, with high mutation efficiency at both loci, 13.79%, 15.7%, respectively.

Figure 3:
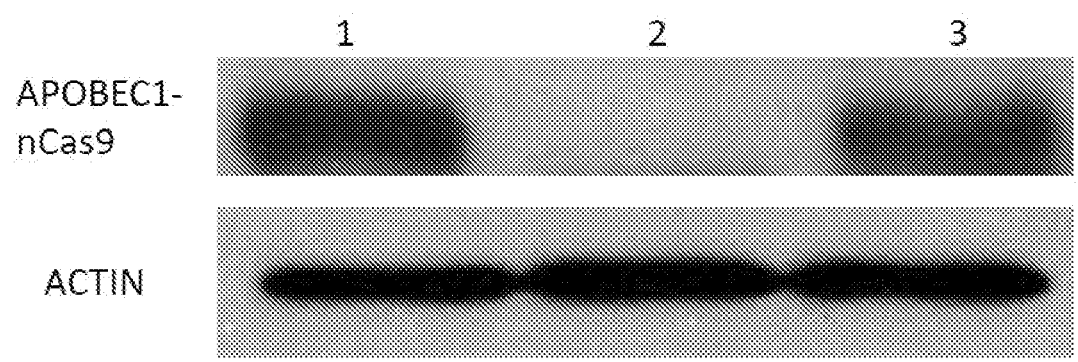
FIG. 3: Expression analysis of APOBEC1-nCas9 protein.

Plant proteins were extracted from three transgenic plants obtained with the SU systems according to the conventional operation, and western blot experiment was carried out using Anti-CRISPR-Cas9 antibody (abcam, ab204448). The internal control is Actin. As shown in FIG. 3, APOBEC1-nCas9 was not mutated in the first and third plants (first and third lanes), and the second plant was homozygous for APOBEC1-nCas9 point mutation (second lane), in which APOBEC1-nCas9 protein is not expressed.

TABLE 2

Editing efficiency of the pSU-PBE system

| Gene | Mutation at target site (number of plants) | Homozygous Cas9 mutation (number of plants) | Total Plants | SU mutation efficiency |
| --- | --- | --- | --- | --- |
| ALS | 26 (89%) | 4 (14%) | 29 | 4/29 = 13.79% |
| NRT | 34 (67%) | 8 (16%) | 51 | 8/51 = 15.7% |

REFERENCES

[1] Komor A C, Kim Y B, Packer M S, Zuris J A, Liu D R. Programmable editing of a target base in genomic DNA without double-stranded DNA cleavage. Nature, 2016, 533 (7603): 420-424.
[2] Ma Y Q, Zhang J Y, Yin W J, Zhang Z C, Song Y, Chang X. Targeted AID-mediated mutagenesis (TAM) enables efficient genomic diversification in mammalian cells. Nat Methods, 2016, 13(12): 1029-1035.
[3] Nishida K, Arazoe T, Yachie N, Banno S, Kakimoto M, Tabata M, Mochizuki M, Miyabe A, Araki M, Hara K Y, Shimatani Z, Kondo A. Targeted nucleotide editing using hybrid prokaryotic and vertebrate adaptive immune systems. Science, 2016, 353(6305): aaf8729.
[4] Hess G T, Frésard L, Han K, Lee C H, Li A, Cimprich K A, Montgomery S B, Bassik M C. Directed evolution using dCas9-targeted somatic hypermutation in mammalian cells. Nat Methods, 2016: 13(12): 1036-1042.

The invention claimed is:

1. A genome editing system for site-directed modification of at least one genomic target sequence in the genome of a cell, comprising:
   1) an expression construct comprising a coding sequence of a gRNA targeting the at least one genomic target sequence;
   2) an expression construct comprising a coding sequence of a CRISPR nuclease; and
   3) an expression construct comprising coding sequence for a gRNA targeting a target sequence within the coding sequence of the CRISPR nuclease,
   wherein, upon introduction into the cell, said gRNA targeting the at least one genomic target sequence directs the CRISPR nuclease to said at least one genomic target sequence and results in one or more mutations in the genomic target sequence, and the gRNA targeting a target sequence within the coding sequence of the CRISPR nuclease directs the CRISPR nuclease to said target sequence within the coding sequence of the CRISPR nuclease and results in an inactivating mutation of the CRISPR nuclease,
   wherein the CRISPR nuclease is a single-base editing CRISPR nuclease comprising the amino acid sequence set forth in SEQ ID NO: 1,
   wherein the nucleotide sequence encoding the single-base editing CRISPR nuclease is set forth in SEQ ID NO: 2, and
   wherein the target sequence within the coding sequence of the CRISPR nuclease is set forth in SEQ ID NO: 3.

2. A method of modifying at least one genomic target sequence in the genome of a cell, the method comprising introducing the genome editing system of claim 1 into the cell.

3. The method of claim 2, wherein the cell is selected from the group consisting of:
   mammals selected from the group consisting of humans, mice, rats, monkeys, dogs, pigs, sheep, cows, and cats;
   poultry selected from the group consisting of chicken, ducks, and geese; and
   plants selected from the group consisting of rice, maize, wheat, sorghum, barley, soybean, peanuts, and *Arabidopsis thaliana*.

4. The method of claim 2, wherein the genome editing system is introduced into the cell by a method selected from the group consisting of calcium phosphate transfection, protoplast fusion, electroporation, liposome transfection, microinjection, viral infection, particle bombardment, PEG-mediated protoplast transformation and *Agrobacterium*-mediated transformation.

5. A method of producing a genetically modified cell, the method comprising introducing the genome editing system of claim 1 into a cell.

6. The method of claim 5, wherein the cell is selected from the group consisting of:
   mammals selected from the group consisting of humans, mice, rats, monkeys, dogs, pigs, sheep, cows, and cats;
   poultry selected from the group consisting of chicken, ducks, and geese; and
plants selected from the group consisting of rice, maize, wheat, sorghum, barley, soybean, peanuts, and *Arabidopsis thaliana*.

7. The method of claim 5, wherein the genome editing system is introduced into the cell by a method selected from the group consisting of calcium phosphate transfection, protoplast fusion, electroporation, liposome tra nsfection, microinjection, viral infection, particle bombardment, PEG-mediated protoplast transformation and *Agrobacterium*-mediated transformation.

8. A genetically modified organism comprising the genetically modified cell produced by the method of claim 5, or progeny thereof,
   wherein the genetically modified organism or progeny thereof comprises the one or more mutations in the genomic target sequence.

9. A kit comprising the genome editing system of claim 1, and an instruction for use.

* * * * *

SEQUENCE LISTING

```
<160> NUMBER OF SEQ ID NOS: 4

<210> SEQ ID NO 1
<211> LENGTH: 1736
<212> TYPE: PRT
<213> ORGANISM: Artificial Sequence
<220> FEATURE:
<223> OTHER INFORMATION: APOBEC1-nCas9

<400> SEQUENCE: 1

Pro Lys Lys Lys Arg Lys Val Ser Ser Glu Thr Gly Pro Val Ala Val
1               5                   10                  15

Asp Pro Thr Leu Arg Arg Arg Ile Glu Pro His Glu Phe Glu Val Phe
            20                  25                  30

Phe Asp Pro Arg Glu Leu Arg Lys Glu Thr Cys Leu Leu Tyr Glu Ile
        35                  40                  45

Asn Trp Gly Gly Arg His Ser Ile Trp Arg His Thr Ser Gln Asn Thr
    50                  55                  60

Asn Lys His Val Glu Val Asn Phe Ile Glu Lys Phe Thr Thr Glu Arg
65                  70                  75                  80

Tyr Phe Cys Pro Asn Thr Arg Cys Ser Ile Thr Trp Phe Leu Ser Trp
                85                  90                  95

Ser Pro Cys Gly Glu Cys Ser Arg Ala Ile Thr Glu Phe Leu Ser Arg
            100                 105                 110

Tyr Pro His Val Thr Leu Phe Ile Tyr Ile Ala Arg Leu Tyr His His
        115                 120                 125
```

```
Ala Asp Pro Arg Asn Arg Gln Gly Leu Arg Asp Leu Ile Ser Ser Gly
    130                 135                 140

Val Thr Ile Gln Ile Met Thr Glu Gln Glu Ser Gly Tyr Cys Trp Arg
145                 150                 155                 160

Asn Phe Val Asn Tyr Ser Pro Ser Asn Glu Ala His Trp Pro Arg Tyr
                165                 170                 175

Pro His Leu Trp Val Arg Leu Tyr Val Leu Glu Leu Tyr Cys Ile Ile
                180                 185                 190

Leu Gly Leu Pro Pro Cys Leu Asn Ile Leu Arg Arg Lys Gln Pro Gln
        195                 200                 205

Leu Thr Phe Phe Thr Ile Ala Leu Gln Ser Cys His Tyr Gln Arg Leu
    210                 215                 220

Pro Pro His Ile Leu Trp Ala Thr Gly Leu Lys Ser Gly Ser Glu Thr
225                 230                 235                 240

Pro Gly Thr Ser Glu Ser Ala Thr Pro Glu Leu Lys Asp Lys Lys Tyr
                245                 250                 255

Ser Ile Gly Leu Ala Ile Gly Thr Asn Ser Val Gly Trp Ala Val Ile
                260                 265                 270

Thr Asp Glu Tyr Lys Val Pro Ser Lys Lys Phe Lys Val Leu Gly Asn
    275                 280                 285

Thr Asp Arg His Ser Ile Lys Lys Asn Leu Ile Gly Ala Leu Leu Phe
    290                 295                 300

Asp Ser Gly Glu Thr Ala Glu Ala Thr Arg Leu Lys Arg Thr Ala Arg
305                 310                 315                 320

Arg Arg Tyr Thr Arg Arg Lys Asn Arg Ile Cys Tyr Leu Gln Glu Ile
                325                 330                 335

Phe Ser Asn Glu Met Ala Lys Val Asp Asp Ser Phe Phe His Arg Leu
                340                 345                 350

Glu Glu Ser Phe Leu Val Glu Glu Asp Lys Lys His Glu Arg His Pro
        355                 360                 365

Ile Phe Gly Asn Ile Val Asp Glu Val Ala Tyr His Glu Lys Tyr Pro
    370                 375                 380

Thr Ile Tyr His Leu Arg Lys Lys Leu Val Asp Ser Thr Asp Lys Ala
385                 390                 395                 400

Asp Leu Arg Leu Ile Tyr Leu Ala Leu Ala His Met Ile Lys Phe Arg
                405                 410                 415

Gly His Phe Leu Ile Glu Gly Asp Leu Asn Pro Asp Asn Ser Asp Val
                420                 425                 430

Asp Lys Leu Phe Ile Gln Leu Val Gln Thr Tyr Asn Gln Leu Phe Glu
        435                 440                 445

Glu Asn Pro Ile Asn Ala Ser Gly Val Asp Ala Lys Ala Ile Leu Ser
    450                 455                 460

Ala Arg Leu Ser Lys Ser Arg Arg Leu Glu Asn Leu Ile Ala Gln Leu
465                 470                 475                 480

Pro Gly Glu Lys Lys Asn Gly Leu Phe Gly Asn Leu Ile Ala Leu Ser
                485                 490                 495

Leu Gly Leu Thr Pro Asn Phe Lys Ser Asn Phe Asp Leu Ala Glu Asp
                500                 505                 510

Ala Lys Leu Gln Leu Ser Lys Asp Thr Tyr Asp Asp Asp Leu Asp Asn
        515                 520                 525

Leu Leu Ala Gln Ile Gly Asp Gln Tyr Ala Asp Leu Phe Leu Ala Ala
    530                 535                 540

Lys Asn Leu Ser Asp Ala Ile Leu Leu Ser Asp Ile Leu Arg Val Asn
```

-continued

```
            545                 550                 555                 560

Thr Glu Ile Thr Lys Ala Pro Leu Ser Ala Ser Met Ile Lys Arg Tyr
                        565                 570                 575

Asp Glu His His Gln Asp Leu Thr Leu Leu Lys Ala Leu Val Arg Gln
                        580                 585                 590

Gln Leu Pro Glu Lys Tyr Lys Glu Ile Phe Phe Asp Gln Ser Lys Asn
                        595                 600                 605

Gly Tyr Ala Gly Tyr Ile Asp Gly Gly Ala Ser Gln Glu Glu Phe Tyr
                        610                 615                 620

Lys Phe Ile Lys Pro Ile Leu Glu Lys Met Asp Gly Thr Glu Glu Leu
        625                 630                 635                 640

Leu Val Lys Leu Asn Arg Glu Asp Leu Leu Arg Lys Gln Arg Thr Phe
                        645                 650                 655

Asp Asn Gly Ser Ile Pro His Gln Ile His Leu Gly Glu Leu His Ala
                        660                 665                 670

Ile Leu Arg Arg Gln Glu Asp Phe Tyr Pro Phe Leu Lys Asp Asn Arg
                        675                 680                 685

Glu Lys Ile Glu Lys Ile Leu Thr Phe Arg Ile Pro Tyr Tyr Val Gly
                        690                 695                 700

Pro Leu Ala Arg Gly Asn Ser Arg Phe Ala Trp Met Thr Arg Lys Ser
        705                 710                 715                 720

Glu Glu Thr Ile Thr Pro Trp Asn Phe Glu Glu Val Val Asp Lys Gly
                        725                 730                 735

Ala Ser Ala Gln Ser Phe Ile Glu Arg Met Thr Asn Phe Asp Lys Asn
                        740                 745                 750

Leu Pro Asn Glu Lys Val Leu Pro Lys His Ser Leu Leu Tyr Glu Tyr
                        755                 760                 765

Phe Thr Val Tyr Asn Glu Leu Thr Lys Val Lys Tyr Val Thr Glu Gly
                        770                 775                 780

Met Arg Lys Pro Ala Phe Leu Ser Gly Glu Gln Lys Lys Ala Ile Val
        785                 790                 795                 800

Asp Leu Leu Phe Lys Thr Asn Arg Lys Val Thr Val Lys Gln Leu Lys
                        805                 810                 815

Glu Asp Tyr Phe Lys Lys Ile Glu Cys Phe Asp Ser Val Glu Ile Ser
                        820                 825                 830

Gly Val Glu Asp Arg Phe Asn Ala Ser Leu Gly Thr Tyr His Asp Leu
                        835                 840                 845

Leu Lys Ile Ile Lys Asp Lys Asp Phe Leu Asp Asn Glu Glu Asn Glu
        850                 855                 860

Asp Ile Leu Glu Asp Ile Val Leu Thr Leu Thr Leu Phe Glu Asp Arg
        865                 870                 875                 880

Glu Met Ile Glu Glu Arg Leu Lys Thr Tyr Ala His Leu Phe Asp Asp
                        885                 890                 895

Lys Val Met Lys Gln Leu Lys Arg Arg Arg Tyr Thr Gly Trp Gly Arg
                        900                 905                 910

Leu Ser Arg Lys Leu Ile Asn Gly Ile Arg Asp Lys Gln Ser Gly Lys
                        915                 920                 925

Thr Ile Leu Asp Phe Leu Lys Ser Asp Gly Phe Ala Asn Arg Asn Phe
                        930                 935                 940

Met Gln Leu Ile His Asp Asp Ser Leu Thr Phe Lys Glu Asp Ile Gln
        945                 950                 955                 960

Lys Ala Gln Val Ser Gly Gln Gly Asp Ser Leu His Glu His Ile Ala
                        965                 970                 975
```

```
Asn Leu Ala Gly Ser Pro Ala Ile Lys Lys Gly Ile Leu Gln Thr Val
            980                 985                 990

Lys Val Val Asp Glu Leu Val Lys  Val Met Gly Arg His  Lys Pro Glu
            995                 1000                1005

Asn Ile Val Ile Glu Met Ala Arg Glu Asn Gln Thr Thr Gln Lys
            1010                1015                1020

Gly Gln Lys Asn Ser Arg Glu Arg Met Lys Arg Ile Glu Glu Gly
            1025                1030                1035

Ile Lys Glu Leu Gly Ser Gln Ile Leu Lys Glu His Pro Val Glu
            1040                1045                1050

Asn Thr Gln Leu Gln Asn Glu Lys Leu Tyr Leu Tyr Tyr Leu Gln
            1055                1060                1065

Asn Gly Arg Asp Met Tyr Val Asp Gln Glu Leu Asp Ile Asn Arg
            1070                1075                1080

Leu Ser Asp Tyr Asp Val Asp His Ile Val Pro Gln Ser Phe Leu
            1085                1090                1095

Lys Asp Asp Ser Ile Asp Asn Lys Val Leu Thr Arg Ser Asp Lys
            1100                1105                1110

Asn Arg Gly Lys Ser Asp Asn Val Pro Ser Glu Glu Val Val Lys
            1115                1120                1125

Lys Met Lys Asn Tyr Trp Arg Gln Leu Leu Asn Ala Lys Leu Ile
            1130                1135                1140

Thr Gln Arg Lys Phe Asp Asn Leu Thr Lys Ala Glu Arg Gly Gly
            1145                1150                1155

Leu Ser Glu Leu Asp Lys Ala Gly Phe Ile Lys Arg Gln Leu Val
            1160                1165                1170

Glu Thr Arg Gln Ile Thr Lys His Val Ala Gln Ile Leu Asp Ser
            1175                1180                1185

Arg Met Asn Thr Lys Tyr Asp Glu Asn Asp Lys Leu Ile Arg Glu
            1190                1195                1200

Val Lys Val Ile Thr Leu Lys Ser Lys Leu Val Ser Asp Phe Arg
            1205                1210                1215

Lys Asp Phe Gln Phe Tyr Lys Val Arg Glu Ile Asn Asn Tyr His
            1220                1225                1230

His Ala His Asp Ala Tyr Leu Asn Ala Val Val Gly Thr Ala Leu
            1235                1240                1245

Ile Lys Lys Tyr Pro Lys Leu Glu Ser Glu Phe Val Tyr Gly Asp
            1250                1255                1260

Tyr Lys Val Tyr Asp Val Arg Lys Met Ile Ala Lys Ser Glu Gln
            1265                1270                1275

Glu Ile Gly Lys Ala Thr Ala Lys Tyr Phe Phe Tyr Ser Asn Ile
            1280                1285                1290

Met Asn Phe Phe Lys Thr Glu Ile Thr Leu Ala Asn Gly Glu Ile
            1295                1300                1305

Arg Lys Arg Pro Leu Ile Glu Thr Asn Gly Glu Thr Gly Glu Ile
            1310                1315                1320

Val Trp Asp Lys Gly Arg Asp Phe Ala Thr Val Arg Lys Val Leu
            1325                1330                1335

Ser Met Pro Gln Val Asn Ile Val Lys Lys Thr Glu Val Gln Thr
            1340                1345                1350

Gly Gly Phe Ser Lys Glu Ser Ile Leu Pro Lys Arg Asn Ser Asp
            1355                1360                1365
```

Lys Leu Ile Ala Arg Lys Lys Asp Trp Asp Pro Lys Lys Tyr Gly
1370             1375                 1380

Gly Phe Asp Ser Pro Thr Val Ala Tyr Ser Val Leu Val Val Ala
1385             1390                 1395

Lys Val Glu Lys Gly Lys Ser Lys Lys Leu Lys Ser Val Lys Glu
1400             1405                 1410

Leu Leu Gly Ile Thr Ile Met Glu Arg Ser Ser Phe Glu Lys Asn
1415             1420                 1425

Pro Ile Asp Phe Leu Glu Ala Lys Gly Tyr Lys Glu Val Lys Lys
1430             1435                 1440

Asp Leu Ile Ile Lys Leu Pro Lys Tyr Ser Leu Phe Glu Leu Glu
1445             1450                 1455

Asn Gly Arg Lys Arg Met Leu Ala Ser Ala Gly Glu Leu Gln Lys
1460             1465                 1470

Gly Asn Glu Leu Ala Leu Pro Ser Lys Tyr Val Asn Phe Leu Tyr
1475             1480                 1485

Leu Ala Ser His Tyr Glu Lys Leu Lys Gly Ser Pro Glu Asp Asn
1490             1495                 1500

Glu Gln Lys Gln Leu Phe Val Glu Gln His Lys His Tyr Leu Asp
1505             1510                 1515

Glu Ile Ile Glu Gln Ile Ser Glu Phe Ser Lys Arg Val Ile Leu
1520             1525                 1530

Ala Asp Ala Asn Leu Asp Lys Val Leu Ser Ala Tyr Asn Lys His
1535             1540                 1545

Arg Asp Lys Pro Ile Arg Glu Gln Ala Glu Asn Ile Ile His Leu
1550             1555                 1560

Phe Thr Leu Thr Asn Leu Gly Ala Pro Ala Ala Phe Lys Tyr Phe
1565             1570                 1575

Asp Thr Thr Ile Asp Arg Lys Arg Tyr Thr Ser Thr Lys Glu Val
1580             1585                 1590

Leu Asp Ala Thr Leu Ile His Gln Ser Ile Thr Gly Leu Tyr Glu
1595             1600                 1605

Thr Arg Ile Asp Leu Ser Gln Leu Gly Gly Asp Lys Arg Pro Ala
1610             1615                 1620

Ala Thr Lys Lys Ala Gly Gln Ala Lys Lys Lys Thr Arg Asp
1625             1630                 1635

Ser Gly Gly Ser Thr Asn Leu Ser Asp Ile Ile Glu Lys Glu Thr
1640             1645                 1650

Gly Lys Gln Leu Val Ile Gln Glu Ser Ile Leu Met Leu Pro Glu
1655             1660                 1665

Glu Val Glu Glu Val Ile Gly Asn Lys Pro Glu Ser Asp Ile Leu
1670             1675                 1680

Val His Thr Ala Tyr Asp Glu Ser Thr Asp Glu Asn Val Met Leu
1685             1690                 1695

Leu Thr Ser Asp Ala Pro Glu Tyr Lys Pro Trp Ala Leu Val Ile
1700             1705                 1710

Gln Asp Ser Asn Gly Glu Asn Lys Ile Lys Met Leu Ser Gly Gly
1715             1720                 1725

Ser Pro Lys Lys Lys Arg Lys Val
1730             1735

<210> SEQ ID NO 2
<211> LENGTH: 5211
<212> TYPE: DNA

<213> ORGANISM: Artificial Sequence
<220> FEATURE:
<223> OTHER INFORMATION: APOBEC1-nCas9 encoding sequence variant

<400> SEQUENCE: 2

```
atgccgaaga agaagcgcaa ggtgtccagc gagacgggcc cagtggctgt cgacccaacg      60
ctgcgcaggc gcatcgagcc gcacgagttc gaggtcttct tcgaccccag ggagctgcgc     120
aaggagacgt gcctcctgta cgagatcaac tggggcggca ggcactccat ctggaggcac     180
accagccaga acacgaacaa gcacgtggag gtcaacttca tcgagaagtt caccacggag     240
aggtacttct gcccgaacac ccgctgctcc atcacgtggt cctgtcctg  gagcccctgc     300
ggcgagtgct ccagggcgat caccgagttc ctcagccgct acccgcacgt gacgctgttc     360
atctacatcg ctaggctcta ccaccacgct gaccccagga caggcaggg  cctccgcgac     420
ctgatctcca gcggcgtgac catccagatc atgacggagc aggagtccgg ctactgctgg     480
aggaacttcg tcaactactc cccaagcaac gaggctcact ggccgaggta cccacacctc     540
tgggtgcgcc tctacgtgct cgagctgtac tgcatcatcc tcggcctgcc gccctgcctc     600
aacatcctga ggcgcaagca gccccagctg accttcttca cgatcgccct ccagagctgc     660
cactaccaga ggctcccacc acacatcctg tgggcgaccg gctcaagtc  cggcagcgag     720
acgccaggca cgtccgagag cgctacgcca gagctgaagg acaagaagta ctcgatcggc     780
ctcgccattg gactaactc  tgttggctgg gccgtgatca ccgacgagta caaggtgccc     840
tcaaagaagt tcaaggtcct gggcaacacc gatcggcatt ccatcaagaa gaatctcatt     900
ggcgctctcc tgttcgacag cggcgagacg gctgaggcta cgcggctcaa cgcaccgct      960
cgacgacgat atacgagaag gaagaatcgc atctgctacc tgcaggagat tttctccaac    1020
gagatggcga aggttgacga ttcttcttc  cacaggctgg aggagtcatt cctcgtggag    1080
gaggataaga agcacgagcg gcatccaatc ttcggcaaca ttgtcgacga ggttgcctac    1140
cacgagaagt accctacgat ctaccatctg cggaagaagc tcgtggactc cacagataag    1200
gcggacctcc gcctgatcta cctcgctctg gcccacatga ttaagttcag gggccatttc    1260
ctgatcgagg ggatctcaa  cccggacaat agcgatgttg acaagctgtt catccagctc    1320
gtgcagacgt acaaccagct cttcgaggag aaccccatta atgcgtcagg cgtcgacgcg    1380
aaggctatcc tgtccgctag gctctcgaag tctcggcgcc tcgagaacct gatcgcccag    1440
ctgccgggcg agaagaagaa cggcctgttc gggaatctca ttgcgctcag cctggggctc    1500
acgcccaact tcaagtcgaa tttcgatctc gctgaggacg ccaagctgca gctctccaag    1560
gacacatacg acgatgacct ggataacctc ctggcccaga tcggcgatca gtacgcggac    1620
ctgttcctcg ctgccaagaa tctgtcggac gccatcctcc tgtctgatat tctcagggtg    1680
aacaccgaga ttacgaaggc tccgctctca gcctccatga tcaagcgcta cgacgagcac    1740
catcaggatc tgaccctcct gaaggcgctg gtcaggcagc agctccccga agtacaag     1800
gagatcttct tcgatcagtc gaagaacggc tacgctgggt acattgacgg cggggcctct    1860
caggaggagt tctacaagtt catcaagccg attctggaga gatggacgg  cacggaggag    1920
ctgctggtga agctcaatcg cgaggacctc ctgaggaagc agcggacatt cgataacggc    1980
agcatcccac accagattca tctcgggga  ctgcacgcta tcctgaggag caggaggac    2040
ttctacccctt tcctcaagga taaccgcgag aagatcgaga agattctgac tttcaggatc    2100
ccgtactacg tcgccccact cgctaggggc aactcccgct tcgcttggat gacccgcaag    2160
tcagaggaga cgatcacgcc gtggaacttc gaggaggtgg tcgacaaggg cgctagcgct    2220
```

```
cagtcgttca tcgagaggat gacgaatttc gacaagaacc tgccaaatga gaaggtgctc    2280
cctaagcact cgctcctgta cgagtacttc acagtctaca acgagctgac taaggtgaag    2340
tatgtgaccg agggcatgag gaagccggct ttcctgtctg gggagcagaa gaaggccatc    2400
gtggacctcc tgttcaagac caaccggaag gtcacggtta agcagctcaa ggaggactac    2460
ttcaagaaga ttgagtgctt cgattcggtc gagatctctg gcgttgagga ccgcttcaac    2520
gcctccctgg ggacctacca cgatctcctg aagatcatta aggataagga cttcctggac    2580
aacgaggaga atgaggatat cctcgaggac attgtgctga cactcactct gttcgaggac    2640
cgggagatga tcgaggagcg cctgaagact tacgcccatc tcttcgatga caaggtcatg    2700
aagcagctca agaggaggag gtacaccggc tgggggaggc tgagcaggaa gctcatcaac    2760
ggcattcggg acaagcagtc cgggaagacg atcctcgact tcctgaagag cgatggcttc    2820
gcgaaccgca atttcatgca gctgattcac gatgacagcc tcacattcaa ggaggatatc    2880
cagaaggctc aggtgagcgg ccaggggac tcgctgcacg agcatatcgc gaacctcgct    2940
ggctcgccag ctatcaagaa ggggattctg cagaccgtga aggttgtgga cgagctggtg    3000
aaggtcatgg gcaggcacaa gcctgagaac atcgtcattg agatggcccg ggagaatcag    3060
accacgcaga agggccagaa gaactcacgc gagaggatga agaggatcga ggagggcatt    3120
aaggagctgg ggtcccagat cctcaaggag cacccggtgg agaacacgca gctgcagaat    3180
gagaagctct acctgtacta cctccagaat ggccgcgata tgtatgtgga ccaggagctg    3240
gatattaaca ggctcagcga ttacgacgtc gatcatatcg ttccacagtc attcctgaag    3300
gatgactcca ttgacaacaa ggtcctcacc aggtcggaca agaaccgggg caagtctgat    3360
aatgttcctt cagaggaggt cgttaagaag atgaagaact actggcgcca gctcctgaat    3420
gccaagctga tcacgcagcg gaagttcgat aacctcacaa aggctgagag gggcgggctc    3480
tctgagctgg acaaggcggg cttcatcaag aggcagctgg tcgagacacg gcagatcact    3540
aagcacgttg cgcagattct cgactcacgg atgaacacta agtacgatga aatgacaag    3600 ctgatccgcg aggtgaaggt catcaccctg aagtcaaagc tcgtctccga cttcaggaag    3660
gatttccagt tctacaaggt tcgggagatc aacaattacc accatgccca tgacgcgtac    3720
ctgaacgcgg tggtcggcac agctctgatc aagaagtacc caaagctcga gagcgagttc    3780
gtgtacgggg actacaaggt ttacgatgtg aggaagatga tcgccaagtc ggagcaggag    3840
attggcaagg ctaccgccaa gtacttcttc tactctaaca ttatgaattt cttcaagaca    3900
gagatcactc tggccaatgg cgagatccgg aagcgccccc tcatcgagac gaacggcgag    3960
acgggggaga tcgtgtggga caagggcagg gatttcgcga ccgtcaggaa ggttctctcc    4020
atgccacaag tgaatatcgt caagaagaca gaggtccaga ctggcgggtt ctctaaggag    4080
tcaattctgc ctaagcggaa cagcgacaag ctcatcgccc gcaagaagga ctgggatccg    4140
aagaagtacg gcgggttcga cagccccact gtggcctact cggtcctggt tgtggcgaag    4200
gttgagaagg gcaagtccaa gaagctcaag agcgtgaagg agctgctggg gatcacgatt    4260
atggagcgct ccagcttcga gaagaacccg atcgatttcc tggaggcgaa gggctacaag    4320
gaggtgaaga aggacctgat cattaagctc cccaagtact cactcttcga gctggagaac    4380
ggcaggaagc ggatgctggc ttccgctggc gagctgcaga aggggaacga gctggctctg    4440
ccgtccaagt atgtgaactt cctctacctg gcctcccact acgagaagct caagggcagc    4500
cccgaggaca acgagcagaa gcagctgttc gtcgagcagc acaagcatta cctcgacgag    4560
```

```
atcattgagc agatttccga gttctccaag cgcgtgatcc tggccgacgc gaatctggat      4620
aaggtcctct ccgcgtacaa caagcaccgc gacaagccaa tcaggagca ggctgagaat       4680 atcattcatc tcttcaccct gacgaacctc ggcgcccctg ctgctttcaa gtacttcgac     4740
acaactatcg atcgcaagag gtacacaagc actaaggagg tcctggacgc gacccctcatc   4800 caccagtcga ttaccggcct ctacgagacg cgcatcgacc tgtctcagct cgggggcgac    4860
aagcggccag cggcgacgaa gaaggcgggg caggcgaaga agaagaagac ccgcgactcc    4920
ggcggcagca cgaacctctc cgacatcatc gagaaggaga cgggcaagca gctcgtgatc    4980
caggagagca tcctcatgct gccggaggag gtggaggagg tcatcggcaa caagcccgag    5040
tccgacatcc tcgtgcacac cgcctacgac gagtccacgg acgagaacgt catgctcctg    5100
acgagcgacg ctccagagta caagccatgg gctctcgtga tccaggacag caacggcgag    5160
aacaagatca agatgctgtc cggcggctcc ccgaagaaga agcgcaaggt c              5211

<210> SEQ ID NO 3
<211> LENGTH: 23
<212> TYPE: DNA
<213> ORGANISM: Artificial Sequence
<220> FEATURE:
<223> OTHER INFORMATION: target sequence

<400> SEQUENCE: 3
ctcgacgacg atatacgaga agg                                              23

<210> SEQ ID NO 4
<211> LENGTH: 4764
<212> TYPE: DNA
<213> ORGANISM: Artificial Sequence
<220> FEATURE:
<223> OTHER INFORMATION: APOBEC1-nCas9 encoding sequence

<400> SEQUENCE: 4
atgacggagc aggagtccgg ctactgctgg aggaacttcg tcaactactc cccaagcaac       60
gaggctcact ggccgaggta cccacacctc tgggtgcgcc tctacgtgct cgagctgtac      120
tgcatcatcc tcggcctgcc gccctgcctc aacatcctga ggcgcaagca gccccagctg     180
accttcttca cgatcgccct ccagagctgc cactaccaga ggctcccacc acacatcctg     240
tgggcgaccg gctcaagtc cggcagcgag acgccaggca cgtccgagag cgctacgcca     300
gagctgaagg acaagaagta ctcgatcggc ctcgccattg gactaactc tgttggctgg     360 gccgtgatca ccgacgagta caaggtgccc tcaaagaagt tcaaggtcct gggcaacacc    420
gatcggcatt ccatcaagaa gaatctcatt ggcgctctcc tgttcgacag cggcgagacg    480
gctgaggcta cgcggctcaa cgcaccgcc cgcaggcggt acacgcgcag gaagaatcgc     540
atctgctacc tgcaggagat tttctccaac gagatggcga aggttgacga ttctttcttc     600
cacaggctgg aggagtcatt cctcgtggag gaggataaga agcacgagcg gcatccaatc    660
ttcggcaaca ttgtcgacga ggttgcctac acgagaagt acccctacgat ctaccatctg     720 cggaagaagc tcgtggactc cacagataag gcggacctcc gcctgatcta cctcgctctg    780
gcccacatga ttaagttcag gggccatttc ctgatcgagg ggatctcaa cccggacaat     840 agcgatgttg acaagctgtt catccagctc gtgcagacgt acaaccagct cttcgaggag    900 aacccccatta atgcgtcagg cgtcgacgcg aaggctatcc tgtccgctag gctctcgaag    960
tctcggcgcc tcgagaacct gatcgcccag ctgccgggcg agaagaagaa cggcctgttc   1020
gggaatctca ttgcgctcag cctggggctc acgcccaact tcaagtcgaa tttcgatctc   1080
```

```
gctgaggacg ccaagctgca gctctccaag gacacatacg acgatgacct ggataacctc    1140
ctggcccaga tcggcgatca gtacgcggac ctgttcctcg ctgccaagaa tctgtcggac    1200
gccatcctcc tgtctgatat tctcagggtg aacaccgaga ttacgaaggc tccgctctca    1260
gcctccatga tcaagcgcta cgacgagcac catcaggatc tgaccctcct gaaggcgctg    1320
gtcaggcagc agctccccga gaagtacaag gagatcttct tcgatcagtc gaagaacggc    1380
tacgctgggt acattgacgg cggggcctct caggaggagt tctacaagtt catcaagccg    1440
attctggaga gatggacgg cacggaggag ctgctggtga agctcaatcg cgaggacctc    1500
ctgaggaagc agcggacatt cgataacggc agcatcccac accagattca tctcggggag    1560
ctgcacgcta tcctgaggag gcaggaggac ttctacccct tcctcaagga taaccgcgag    1620
aagatcgaga gattctgac tttcaggatc ccgtactacg tcggcccact cgctaggggc    1680
aactcccgct tcgcttggat gacccgcaag tcagaggaga cgatcacgcc gtggaacttc    1740
gaggaggtgg tcgacaaggg cgctagcgct cagtcgttca tcgagaggat gacgaatttc    1800
gacaagaacc tgccaaatga aaggtgctc cctaagcact cgctcctgta cgagtacttc    1860
acagtctaca acgagctgac taaggtgaag tatgtgaccg agggcatgag gaagccggct    1920
ttcctgtctg gggagcagaa gaaggccatc gtggacctcc tgttcaagac caaccggaag    1980
gtcacggtta agcagctcaa ggaggactac ttcaagaaga ttgagtgctt cgattcggtc    2040
gagatctctg gcgttgagga ccgcttcaac gcctccctgg ggacctacca cgatctcctg    2100
aagatcatta aggataagga cttcctggac aacgaggaga tgaggatat cctcgaggac    2160
attgtgctga cactcactct gttcgaggac cgggagatga tcgaggagcg cctgaagact    2220
tacgcccatc tcttcgatga caaggtcatg aagcagctca agaggaggag gtacaccggc    2280
tgggggaggc tgagcaggaa gctcatcaac ggcattcggg acaagcagtc cgggaagacg    2340
atcctcgact tcctgaagag cgatggcttc gcgaaccgca atttcatgca gctgattcac    2400
gatgacagcc tcacattcaa ggaggatatc cagaaggctc aggtgagcgg ccaggggac    2460
tcgctgcacg agcatatcgc gaacctcgct ggctcgccag ctatcaagaa ggggattctg    2520
cagaccgtga aggttgtgga cgagctggtg aaggtcatgg gcaggcacaa gcctgagaac    2580
atcgtcattg agatggcccg ggagaatcag accacgcaga agggccagaa gaactcacgc    2640
gagaggatga gaggatcga ggagggcatt aaggagctgg ggtcccagat cctcaaggag    2700
caccggtgg agaacacgca gctgcagaat gagaagctct acctgtacta cctccagaat    2760
ggccgcgata tgtatgtgga ccaggagctg gatattaaca ggctcagcga ttacgacgtc    2820
gatcatatcg ttccacagtc attcctgaag gatgactcca ttgacaacaa ggtcctcacc    2880
aggtcggaca agaaccgggg caagtctgat aatgttcctt cagaggaggt cgttaagaag    2940
atgaagaact actggcgcca gctcctgaat gccaagctga tcacgcagcg gaagttcgat    3000
aacctcacaa aggctgagag gggcgggctc tctgagctgg acaaggcggg cttcatcaag    3060
aggcagctgg tcgagacacg gcagatcact aagcacgttg cgcagattct cgactcacgg    3120
atgaacacta gtacgatga aatgacaag ctgatccgcg aggtgaaggt catcaccctg    3180
aagtcaaagc tcgtctccga cttcaggaag gatttccagt tctacaaggt tcgggagatc    3240
aacaattacc accatgccca tgacgcgtac ctgaacgcgg tggtcggcac agctctgatc    3300
aagaagtacc caaagctcga gagcgagttc gtgtacgggg actacaaggt ttacgatgtg    3360
aggaagatga tcgccaagtc ggagcaggag attggcaagg ctaccgccaa gtacttcttc    3420
```

-continued

```
tactctaaca ttatgaattt cttcaagaca gagatcactc tggccaatgg cgagatccgg    3480
aagcgccccc tcatcgagac gaacggcgag acggggggaga tcgtgtggga caagggcagg   3540
gatttcgcga ccgtcaggaa ggttctctcc atgccacaag tgaatatcgt caagaagaca   3600
gaggtccaga ctggcgggtt ctctaaggag tcaattctgc ctaagcggaa cagcgacaag   3660
ctcatcgccc gcaagaagga ctgggatccg aagaagtacg gcgggttcga cagccccact   3720
gtggcctact cggtcctggt tgtggcgaag gttgagaagg gcaagtccaa gaagctcaag   3780
agcgtgaagg agctgctggg gatcacgatt atggagcgct ccagcttcga gaagaacccg   3840
atcgatttcc tggaggcgaa gggctacaag gaggtgaaga aggacctgat cattaagctc   3900
cccaagtact cactcttcga gctggagaac ggcaggaagc ggatgctggc ttccgctggc   3960
gagctgcaga aggggaacga gctggctctg ccgtccaagt atgtgaactt cctctacctg   4020
gcctcccact acgagaagct caagggcagc cccgaggaca acgagcagaa gcagctgttc   4080
gtcgagcagc acaagcatta cctcgacgag atcattgagc agatttccga gttctccaag   4140
cgcgtgatcc tggccgacgc gaatctggat aaggtcctct ccgcgtacaa caagcaccgc   4200
gacaagccaa tcagggagca ggctgagaat atcattcatc tcttcaccct gacgaacctc   4260 ggcgccctg ctgctttcaa gtacttcgac acaactatcg atcgcaagag gtacacaagc    4320
actaaggagg tcctggacgc gaccctcatc caccagtcga ttaccggcct ctacgagacg   4380
cgcatcgacc tgtctcagct cggggggcgac aagcggccag cggcgacgaa gaaggcgggg  4440
caggcgaaga agaagaagac ccgcgactcc ggcggcagca cgaacctctc cgacatcatc   4500
gagaaggaga cgggcaagca gctcgtgatc caggagagca tcctcatgct gccggaggag   4560
gtggaggagg tcatcggcaa caagcccgag tccgacatcc tcgtgcacac cgcctacgac   4620
gagtccacgg acgagaacgt catgctcctg acgagcgacg ctccagagta caagccatgg   4680
gctctcgtga tccaggacag caacggcgag aacaagatca agatgctgtc cggcggctcc   4740
ccgaagaaga agcgcaaggt ctga                                          4764
```